US008124383B2

(12) United States Patent
Lo et al.

(10) Patent No.: US 8,124,383 B2
(45) Date of Patent: *Feb. 28, 2012

(54) METHODS AND KITS FOR DIAGNOSIS, PROGNOSIS OR MONITORING OF EPSTEIN-BARR VIRUS (EBV)—ASSOCIATED CANCER

(75) Inventors: Yuk Ming Dennis Lo, Hong Kong (CN); Kwan Chee Allen Chan, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/909,688

(22) Filed: Oct. 21, 2010

(65) Prior Publication Data

US 2011/0033841 A1    Feb. 10, 2011

Related U.S. Application Data

(63) Continuation of application No. 11/711,419, filed on Feb. 26, 2007, now Pat. No. 7,842,482.

(51) Int. Cl.
*C12P 19/34* (2006.01)

(52) U.S. Cl. ..................................................... 435/91.2

(58) Field of Classification Search ................. 435/91.1, 435/91.2, 91.21
See application file for complete search history.

(56) References Cited

U.S. PATENT DOCUMENTS

| | | | | |
|---|---|---|---|---|
| 6,506,553 | B1 | 1/2003 | Smith et al. | 435/5 |
| 6,753,137 | B2 | 6/2004 | Lo et al. | 435/5 |
| 2003/0228575 | A1 | 12/2003 | Yeung et al. | 435/5 |
| 2004/0005551 | A1 | 1/2004 | Lo et al. | 435/5 |
| 2004/0063091 | A1 | 4/2004 | Smith et al. | 435/5 |
| 2006/0183108 | A1 | 8/2006 | Melkonyan et al. | 435/5 |

FOREIGN PATENT DOCUMENTS

| | | |
|---|---|---|
| WO | 02061148 | 8/2002 |
| WO | 2006/089203 | 8/2006 |

OTHER PUBLICATIONS

Botezatu et al., "Genetic Analysis of DNA Excreted in Urine: A New Approach for Detecting Specific Genomic DNA Sequences from Cells Dying in an Organism," *Clinical Chemistry* 46(8):1078-1084, 2000.

Bryzgunova et al., "Isolation and Comparative Study of Cell-Free Nucleic Acids from Human Urine," *Annals New York Academy of Sciences 1075*:334-340, 2006.

Chan et al., "Plasma Epstein-Barr Virus DNA and Residual Disease After Radiotherapy for Undifferentiated Nasopharyngeal Carcinoma," *Journal of the National Cancer Institute* 94(21):1614-1619, Nov. 6, 2002.

Chan et al., "Size Distributions of Maternal and Fetal DNA in Maternal Plasma," *Clinical Chemistry* 50(1):88-92, 2004.

Chen et al., "Detection of Epstein-Barr Virus Genome in Nasopharyngeal Carcinoma by In situ DNA Hybridization," *Intervirology* 36:91-98, 1993.

Dickens, P., "Epstein-Barr virus DNA in nasopharyngeal carcinomas from Chinese patients in Hong Kong," *J. Clin. Pathol.* 45:396-397, 1992.

Jones et al., "Clustered repeat sequences in the genome of Epstein Barr virus," *Nucleic Acids Research* 11(12):3919-3937, 1983.

Krishna et al., "Serum EBV DNA as a Biomarker in Primary Nasopharyngeal Carcinoma of Indian Origin," *Jpn J Clin Oncol* 34(6):307-311, 2004.

Laxman et al., "Noninvasive Detection of *TMPRSS2:ERG* Fusion Transcripts in the Urine of Men with Prostate Cancer," *Neoplasia* 8(10):885-888, Oct. 2006.

Lei et al., "Quantitative analysis of circulating cell-free Epstein-Barr virus (EBV) DNA levels in patients with EBV-associated lymphoid malignancies," *British Journal of Haematology* 111:239-246, 2000.

Lo et al., "Quantitative Analysis of Cell-free Epstein-Barr Virus DNA in Plasma of Patients with Nasopharyngeal Carcinoma," *Cancer Research* 59:1188-1191, Mar. 15, 1999.

Lo et al., "Molecular Prognostication of Nasopharyngeal Carcinoma by Quantitative Analysis of Circulating Epstein-Barr Virus DNA," *Cancer Research* 60:6878-6881, Dec. 15, 2000.

Lo et al., "Circulating Epstein-Barr Virus DNA in the Serum of Patients with Gastric Carcinoma," *Clinical Cancer Research* 7:1856-1859, Jul. 2001.

Stevens et al., "Diagnostic Value of Measuring Epstein-Barr Virus (EBV) DNA Load and Carcinoma-Specific Viral mRNA in Relation to Anti-EBV Immunoglobulin A (IgA) and IgG Antibody Levels in Blood of Nasopharyngeal Carcinoma Patients from Indonesia," *Journal of Clinical Microbiology* 43(7):3066-3073, Jul. 2005.

*Primary Examiner* — Gary Benzion
*Assistant Examiner* — Cynthia Wilder
(74) *Attorney, Agent, or Firm* — Seed IP Law Group PLLC

(57) ABSTRACT

Disclosed is a non-invasive method for diagnosis, prognosis or monitoring of Epstein-Barr virus (EBV)-associated cancer by detecting and/or quantifying EBV associated nucleic acid fragments in a urine sample from an individual. Kits for diagnosis, prognosis or monitoring of cancer are also disclosed.

21 Claims, 2 Drawing Sheets

METHODS AND KITS FOR DIAGNOSIS, PROGNOSIS OR MONITORING OF EPSTEIN-BARR VIRUS (EBV)—ASSOCIATED CANCER

CROSS-REFERENCE TO RELATED APPLICATION

This application is a continuation of U.S. patent application Ser. No. 11/711,419, filed Feb. 26, 2007 (now U.S. Pat. No. 7,842,482). This application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200167_403C1_SEQUENCE_LISTING.txt. The text file is 2 KB, was created on Oct. 21, 2010, and is being submitted electronically via EFS-Web, concurrent with the filing of the specification.

FIELD OF THE INVENTION

The present invention generally relates to methods and kits for diagnosis, prognosis or monitoring of a cancer in an individual by detecting and/or quantifying tumor-associated DNA sequences. More specifically, this invention relates to methods and kits for diagnosis, prognosis or monitoring of an Epstein-Barr virus (EBV)-associated cancer by detecting and/or quantifying an EBV DNA sequence in urine.

BACKGROUND OF THE INVENTION

Epstein-Barr virus (EBV) is a ubiquitous human herpesvirus that was first discovered in association with the African form of Burkitt's lymphoma (BL). Subsequently, EBV infection is also found to be strongly associated with nasopharyngeal carcinoma (NPC).

It has been shown that the EBV genome can be detected in almost all NPC tissues collected in Southern China (Chen et al., Intervirology. 36(2):91-8 (1993); Dickens et al., J Clin Pathol. 45(5):396-7 (1992)). Consistent with these results, we have demonstrated that EBV DNA can be detected in the plasma of 96% of NPC patients but only 7% of healthy subjects at a much lower concentration (Lo et al., Cancer Res. 59(6):1188-91 (1999)). Moreover, the level of plasma EBV DNA, measured either before (Lo et al., Cancer Res. 60(24): 6878-81 (2000)) or after treatment (Chan et al., J Natl Cancer Inst. 94(21):1614-9 (2002)), is valuable for predicting the overall and disease-free survival. Similarly, circulating EBV DNA is also useful for the detection and monitoring of other EBV-associated malignancies, for example, lymphoma (Lei et al., Br J. Haematol. 111(1):239-46 (2000)) and gastric carcinoma (Lo et al., Clin Cancer Res. 7(7):1856-9 (2001)).

Although this plasma test is useful for the detection of NPC and is a relatively risk free procedure, it still causes pain and anxiety in patients. However, detection and/or quantification of short EBV associated nucleic acid sequences in a urine sample, as well as uses thereof, have not been disclosed in the art. Accordingly, there is a need for develop an alternative test for diagnosis, prognosis, and/or monitoring of EBV-associated cancers.

SUMMARY OF THE INVENTION

We surprisingly find that the circulating cell-free Epstein-Barr virus (EBV) DNA can pass through the kidney barrier and be detected in urine as a tumor marker for NPC and other EBV-associated malignancies.

According to a first aspect of the present invention, there is provided a method for diagnosis of an EBV-associated cancer in an individual. The method comprises:

(a) obtaining a urine sample from the individual; and (b) detecting an EBV associated nucleic acid sequence in the urine sample, wherein the presence of the EBV associated nucleic acid sequence in the urine sample indicates that the individual is suffering from an EBV-associated cancer.

According to a second aspect of the present invention, there is provided a method for prognosis of an EBV-associated cancer in an individual. The method comprises:

(a) obtaining a urine sample from the individual; and (b) detecting an EBV associated nucleic acid sequence in the urine sample, wherein the presence of the EBV associated nucleic acid sequence in the urine sample indicates a poor prognosis of the EBV-associated cancer.

According to a third aspect of the present invention, there is provided a method for monitoring an EBV-associated cancer in an individual. The method comprises:

(a) obtaining urine samples from the individual at different time points; and (b) detecting and/or quantifying an EBV associated nucleic acid sequence in the urine samples, wherein the presence or an increased level of the EBV associated nucleic acid sequence in the urine samples indicates the progression of the EBV-associated cancer, and the absence or a decreased level of the EBV associated nucleic acid sequence in the urine samples indicates the regression of the EBV-associated cancer.

In a specific embodiment of the method of the invention, step (a) is performed during the time course of a treatment for the EBV-associated cancer, and the absence or a decreased level of the EBV associated nucleic acid sequence in the urine samples indicates the effectiveness of the treatment.

In preferred embodiments of the present invention, the methods described above further comprise the step of analyzing the size of the EBV associated nucleic acid sequence in the urine samples to eliminate false positive cases. In these cases, the EBV associated nucleic acid sequence detected and/or quantified in the urine samples may not be derived from the circulating EBV associated nucleic acid fragments and is relatively intact.

In preferred embodiments of the present invention, the EBV associated nucleic acid sequence described above is derived from at least one DNA fragment of the BamHI-W region of the EBV genome or at least one RNA transcript thereof. Preferably, the DNA fragment or the RNA transcript is less than 180 nucleotides.

According to a fourth aspect of the present invention, there is provided a kit for diagnosis or prognosis of an EBV-associated cancer in an individual. The kit comprises:

a) a first unit for extracting nucleic acid from a urine sample from the individual; and b) a second unit for detecting an EBV associated nucleic acid sequence in the extracted nucleic acid, wherein the second unit comprises at least one pair of primers for amplifying at least one fragment of the BamHI-W region of the EBV genome.

According to a fifth aspect of the present invention, there is provided a kit for monitoring an EBV-associated cancer in an individual. The kit comprises:

a) a plurality of first units for extracting a nucleic acid from a urine sample from the individual; and b) a plurality of second units for detecting and/or quantifying an EBV associated nucleic acid sequence in the extracted nucleic acid, wherein the second unit comprises at least one pair of primers for amplifying at least one fragment of the BamHI-W region of the EBV genome.

In one preferred embodiment, the kit according to the present invention further comprises a device for obtaining a urine sample from an individual.

In some embodiments of the present invention, the EBV associated nucleic acid described above is DNA. In other embodiments, it is RNA.

In some preferred embodiments of the present invention, the EBV associated cancer is a nasopharyngeal carcinoma (NPC), a natural-killer-cell lymphoma (NK-lymphoma) or a gastric carcinoma. In more preferred embodiments, the EBV-associated cancer is a nasopharyngeal carcinoma.

Advantages of the present invention will become more apparent to one of ordinary skill in the art from the following description of the preferred embodiments of the present invention that have been shown and described by way of illustration.

DETAILED DESCRIPTION OF THE INVENTION

Figure 1:
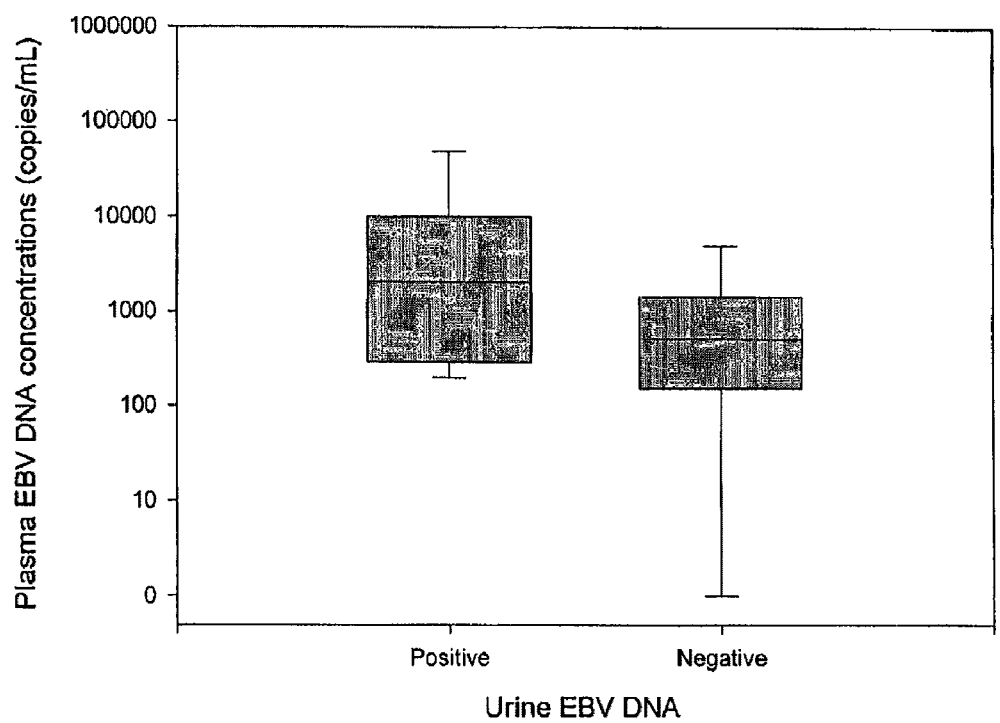
FIG. 1 shows the plasma EBV DNA concentrations in NPC patients according to the detectability of urine EBV DNA.

Unless defined otherwise, all technical and scientific terms used herein have the meaning commonly understood by a person skilled in the art to which this invention belongs.

As described above, the methods of the present invention can be used to diagnose or prognosticate an EBV-associated cancer, such as nasopharyngeal carcinoma (NPC). In these methods, a urine sample is first obtained from an individual and the detection and/or quantification of an EBV DNA sequence in the urine sample is then performed.

A method for monitoring an EBV-associated cancer in an individual is also disclosed. The method comprises steps of (a) obtaining urine samples from the individual at different time points; and (b) detecting and/or quantifying an EBV DNA sequence in the urine samples. A difference in the levels of the EBV DNA sequence in the urine samples is used as an indication of the development of the EBV-associated cancer. For example, the presence or an increased level of the EBV DNA sequence in the urine samples indicates the progression of the EBV-associated cancer, and the absence or a decreased level of the EBV DNA sequence in the urine samples indicates the regression of the EBV-associated cancer. This method is particularly useful for assessing the effectiveness of a treatment for an EBV-associated cancer.

Though the step of obtaining a urine sample from the individual is included in the methods described above, it will be appreciated by those skilled in the art that this step is not necessary in some cases, in which the urine sample has been obtained in advance, for example, at a sampling center.

In preferred embodiments, the detection or quantification of an EBV DNA sequence in the urine sample comprises the steps of (1) extracting DNA from the urine sample; (2) amplifying the EBV DNA sequence from the extracted DNA; and (3) detecting and/or quantifying the amplified EBV DNA sequence.

As used herein, the expression "an EBV DNA sequence" refers to a fragment of the Epstein-Barr virus (EBV) genome (Genbank accession number AJ507799) and typically is a product of the genome DNA degradation. In particular, the EBV DNA sequence according to the present invention comprises at least one fragment of the BamHI-W region of the EBV genome. The BamHI-W region used herein refers to a repeating BamHI-W restriction fragment of the EBV genome as disclosed in Jones et al., Nucleic Acids Res. 11:3919-3937 (1983).

It is understood that a longer DNA sequence will pass through the kidney barrier at a lower rate. Thus, in order to increase the sensitivity of the detection, the size of the selected EBV DNA sequence according to the present invention is no more than 180 bp. Preferably, the size of the target DNA sequence according to the present invention is no more than 76 bp.

As used herein, the term "amplifying" or "amplification" means the production of additional copies of the EBV DNA sequence and is generally carried out using polymerase chain reaction or other technologies well known in the art. With PCR, it is possible to amplify a single copy of an EBV DNA sequence to a level that can be detected by several different methodologies.

In a preferred embodiment of the invention, the step (2) and step (3) are carried out by real-time quantitative PCR (Q-PCR). As used herein, the term "real-time quantitative PCR" or "Q-PCR" refers to a method based on the continuous optical monitoring of the progress of a fluorogenic PCR reaction. In this system, in addition to a pair of amplification primers used in conventional PCR, a dual-labeled fluorogenic hybridization probe is also included. One fluorescent dye serves as a reporter (e.g. FAM), and its emission spectra is quenched by a second fluorescent dye (e.g. TAMRA). During the extension phase of PCR, the 5' to 3' exonuclease activity of Taq DNA polymerase cleaves the reporter from the probe, thus releasing it from the quencher and resulting in an increase in fluorescence. The fluorescence is then used to monitor the amplification process and determine the amount of the original template DNA.

It is found in our research that healthy subjects may occasionally carry EBV DNA in urine. In order to eliminate these false positive cases, the methods of the present invention further include a step of analyzing the size of the EBV DNA sequence present in the urine sample.

In some embodiments, the analyzing of the size of the EBV DNA sequence is carried out by two or more PCR assays or Q-PCR assays. These assays use amplicons of different sizes. Because a longer DNA sequence passes through the kidney barrier at a lower rate, a much lower concentration of the final amplification product will be obtained after the same amplification cycles when larger amplicons are used. If two or more PCR assays or Q-PCR assays targeting an EBV DNA sequence using amplicons of different sizes (e.g., 59 bp and 76 bp) give similar amounts of the final amplification products, the EBV DNA sequence present in the urine may not come from the circulating EBV DNA passed through the kidney barrier. Elimination of these cases renders the methods of the present invention higher reliability for the diagnosis, prognosis or monitoring of NPC and other EBV-associated malignancies.

Alternatively, we can conveniently analyze whether an EBV genome fragment of more than 180 bp is present in the urine sample. As a DNA fragment of more than 180 bp is difficult to pass through the kidney barrier, the presence of an EBV genome fragment of more than 180 bp in the urine sample can be used to exclude the individual from a patient with an EBV-associated cancer.

As described previously, the plasma EBV DNA concentration can be used to diagnose, prognosticate or monitor NPC and other EBV-associated malignancies. It is disclosed in the present invention that there is a good correlation between the plasma and the urine EBV DNA concentrations, i.e. the plasma EBV DNA concentration can be determined by quantifying the urine EBV DNA concentration. Therefore, the assay for the concentration of an EBV DNA sequence in urine is an excellent alternative to the assay in plasma for diagnosing, prognosticating or monitoring NPC and other EBV-associated malignancies.

According to the present invention, the presence of an EBV DNA sequence in a urine sample from an individual can be used as an indication of an EBV-associated cancer, including the stage of the EBV-associated cancer. According to the present invention, the presence of an EBV DNA sequence in a urine sample from an individual can also be used as a poor prognostic factor of an EBV-associated cancer, and for the prediction of the likelihood of overall survival or recurrence for the individual.

When the level of an EBV sequence in the urine of an individual with an EBV-associated cancer is followed for a period of time, the trend of the level reflects the development of the cancer. Generally, an increased level is an indication of the progression of the cancer. The trend of the level of an EBV sequence in the urine can also be used to assess the effectiveness of a treatment for the EBV-associated cancer. The absence or a decreased level of the EBV DNA sequence in the urine sample is a good indication of the effectiveness of the treatment.

EBV DNA is named above as an illustrative example of EBV associated nucleic acid. It is well-known to those of skill in the art that there are other types of nucleic acids, e.g. RNA which are associated with EBV. Accordingly, in certain embodiments, the methods for diagnosis, prognosis and monitoring of EBV-associated cancers comprising detecting EBV associated RNA, such as Epstein-Barr encoded small RNA (EBER) in a urine sample of a human subject.

The present invention also features a kit for diagnosis or prognosis of an EBV-associated cancer in an individual. This kit comprises a) a first unit for extracting DNA from a urine sample; and b) a second unit for detecting and/or quantifying an EBV DNA sequence in the extracted DNA, wherein the second unit comprises at least one pair of primers for amplifying at least one fragment of the BamHI-W region of the EBV genome. The present invention also features a kit for monitoring an EBV-associated cancer in an individual. This kit comprises a) a plurality of first units for extracting DNA from a urine sample; and b) a plurality of second units for detecting and/or quantifying an EBV DNA sequence in the extracted DNA, wherein the second unit comprises at least one pair of primers for amplifying at least one fragment of the BamHI-W region of the EBV genome.

In preferred embodiments, the kits according to the present invention further comprise a device for obtaining a urine sample from an individual. If desired, the kits may also comprise instructions for using the kits. Typically, the second unit of the kits further comprises a probe for a Q-PCR assay. In order to eliminate the false positive cases mentioned above, the kits preferably comprise primers for amplicons of different sizes. For example, the kits include a pair of primers for amplifying an EBV DNA sequence of 180 bp and another pair of primers for amplifying an EBV DNA sequence of 76 bp.

The kit according to the present invention for monitoring an EBV-associated cancer is particularly useful for assessing the effectiveness of a treatment for an EBV-associated cancer, as the absence or a decreased level of the EBV DNA sequence in the urine sample can be used as an indication of the effectiveness of the treatment.

It is apparent to those skilled in the art that the kits according to the present invention can also be used to detect and/or quantify an EBV RNA sequence in a urine sample by using a reverse transcriptase polymerase chain reaction (RT-PCR) assay or a real-time quantitative reverse transcriptase polymerase chain reaction (Q-RT-PCR) assay, for the diagnosis, prognosis or monitoring of an EBV-associated cancer in an individual.

The following examples are provided by way of illustration only and not by way of limitation.

EXAMPLES

44 NPC patients, as well as 70 healthy control subjects, were recruited. DNA was first extracted from urine and plasma samples from the subjects, and the extracted DNA was then amplified for EBV DNA using quantitative real-time PCR targeting the BamHI-W region (Lo 1999 et al.) of the EBV genome, as described below.

Extraction of the DNA Fragments from Urine and Plasma

Ten milliliters of urine were collected from each study subject into an EDTA-containing tube. The urine samples were centrifuged at 1,600 g for 10 minutes at 4° C. The supernatant was filtered with a 0.45 µm filter to remove any remaining cells. DNA was extracted from the urine sample using the Wizard Plus Miniprep DNA Purification Kit (Promega, Madison, Wis.). The filtered supernatant was mixed thoroughly with 15 mL 6M guanidine isothiocyanate (GITC). One milliliter of resin suspension of the DNA purification kit was added to each sample and the mixture was mixed thoroughly on a roller-mixer for 2 hours at room temperature. The urine-resin mixture was then passed through the minicolumn provided in the kit using a 30 mL syringe. Two milliliters of wash solution were then passed through the minicolumn. The remaining wash solution was cleared by a brief centrifugation. One hundred microliters $H_2O$ were added to the minicolumn for the elution of DNA fragments.

The method for extracting DNA fragments from plasma is known in the art, e.g., the method by using a QIAamp Blood Kit (Qiagen, Hilden, Germany) described by Lo et al., Cancer Res. 60(24):6878-81 (2000). In brief, plasma samples were harvested from the patients according to established protocols in the art. The samples were stored at −20° C. until further processing. DNA from plasma samples was extracted using a QIAamp Blood Kit (Qiagen, Hilden, Germany) using the "blood and body fluid protocol" as recommended by the manufacturer. A total of 400-800 µl of the plasma samples were used for DNA extraction per column. The exact amount was documented for the calculation of the target DNA concentration. A final elution volume of 50 µl was used to elute the DNA from the extraction column.

Detection and Quantification of the EBV DNA Fragments

The concentration of urine EBV DNA was determined by two real-time PCR assays both targeting the BamHI-W region of the EBV genome. The amplicon sizes for the two PCR assays were 76 bp and 59 bp. The primers used for the 76 bp assay were 5'-CCCAACACTCCACCACACC-3' (SEQ ID-NO:1) and 5'-TCTTAGGAGCTGTCCGAGGG-3' (SEQ ID NO:2). The primers used for the 59 bp assay were 5'-CCCAGGCACACACTACACACA-3' (SEQ ID NO:3) and 5'-TCTTAGGAGCTGTCCGAGGG-3' (SEQ ID NO:4). The fluorescent probes used for the 76 bp and 59 bp assays were 5'-(FAM)-CACACACTACACACACCCAC-CCGTCTC-(TAMRA)-3' (SEQ ID NO:5) and 5'-(FAM)-CACCCGTCTCAGGG-(MGB)-3' (SEQ ID NO:6), respectively. The PCR reactions were set up in a reaction volume of 50 µL. Each reaction contained 5 µL of 10× buffer A; 300 nM of each of the amplification primers; 25 nM of the corresponding fluorescent probe; 4 mM $MgCl_2$; 200 µM each of dATP, dCTP, and dGTP, 400 µM dUTP; 1.25 units of Ampli-Taq Gold; and 0.5 unit of AmpErase uracil N-glycosylase. Ten microliters of extracted urine DNA were used as a template. An identical thermal profile was used for both PCR systems and was 50° C. for 2 min, 95° C. for 10 min followed by 40 cycles of 95° C. for 15 s and 56° C. for 1 min. A calibration curve was run in parallel with each analysis, using DNA extracted from the EBV-positive cell line, Namalwa, as a standard. Namalwa is a diploid cell line that contains two integrated EBV genomes per cell. Each sample was analyzed in duplicate and the mean value was taken for analysis.

The quantity of the urine EBV DNA can be expressed as a concentration per unit volume of urine, for example copies/mL urine, or expressed as a quantity per the amount of another substance in the urine sample to correct for the concentration of the urine, for example copies/mmol of creatinine.

The Presence or the Level of EBV in the Urine Sample being a Useful Clinical Marker for NPC EBV DNA was detectable in 10 (23%) and 22 (50%) urine samples from NPC patients using the 76 bp and 59 bp assays, respectively (Table 1). The higher detection rate for the 59 bp assay indicates that shorter DNA molecules are more readily filtered through the kidney barrier and be detected in the urine. Consistent with our previous results, the EBV DNA can be detected in almost all of the plasma samples from NPC patients. As shown in Table 1, 41 (93%) plasma samples from NPC patients can be detected using either the 59 bp assay or the 76 bp assay. A further reduction in the size of the target fragment may further increase the sensitivity of EBV associated nucleic acid detection.

TABLE 1

The detection rates of urine EBV DNA in NPC patients using the 59 bp and 76 bp assays

| | | Plasma | |
| --- | --- | --- | --- |
| | | EBV DNA positive | EBV DNA negative |
| 59 bp EBV DNA assay | Urine positive | 22 | 0 |
| | Urine negative | 19 | 3 |
| 76 bp EBV DNA assay | Urine positive | 10 | 0 |
| | Urine negative | 31 | 3 |

70 healthy subjects were also analyzed as controls. EBV DNA was detectable in the plasma of 3 (4%) subjects using the 76 bp assay (Table 2). Their plasma EBV DNA concentrations were 13 copies/mL, 17 copies/mL and 22 copies/mL. These levels were relatively low when compared with the plasma EBV DNA levels of the 44 NPC patients (median: 950 copies/mL). EBV DNA was not detectable in the urine of these three control subjects.

TABLE 2

The detection rates of urine EBV DNA in NPC patients and healthy control subjects using the 59 bp EBV DNA assay

| | | NPC patients | Healthy control subjects |
| --- | --- | --- | --- |
| Urine EBV DNA | Positive | 22 | 2 |
| | Negative | 22 | 68 |

Elimination of False Positive Cases

Surprisingly, EBV DNA was detectable in the urine of two healthy subjects with no detectable plasma EBV DNA at the concentration of 227 copies/mL and 1,280,000 copies/mL.

These two urine samples were further analyzed with 2 real-time PCR assays targeting the BamHI-W region of the EBV genome with amplicon sizes of 76 bp and 180 bp. The urine EBV DNA concentrations for these two subjects were relatively constant using the two assays. For the former subject, the urine EBV DNA concentrations were 333 copies/mL and 243 copies/mL using the 76 bp and 180 bp assays, respectively. For the latter subject, the urine EBV DNA were 1,220,000 copies/mL and 1,073,000 copies/mL using the 76 bp and 180 bp assays, respectively. In contrast, for the NPC patients with detectable urine EBV DNA using both the 59 bp and the 76 bp assays, the median drop in concentration was 93.5%. Urine EBV DNA was not detectable in the urine of the 44 NPC patients using the 180 bp assays. The relatively constant urine EBV DNA concentrations of the two healthy subjects using the two different-sized PCR assays suggests that the EBV DNA molecules detected in their urine were relatively intact when compared with the urine EBV DNA detected in the urine of the NPC patients. One possible explanation would be the presence of intact viral particles in the urine of the two control subjects which may be resulted from active viral replication. Diagnostically, the size of urine EBV DNA can be included in the analysis to increase the specificity of urine EBV DNA analysis.

Correlation Between Plasma and Urine EBV DNA Concentrations

The plasma EBV DNA concentrations of the NPC patients were analyzed using the 76 bp real-time PCR assay. The median plasma EBV DNA concentrations for the patients with detectable and undetectable urine EBV DNA were 2054 copies/mL and 511 copies/mL, respectively (p<0.0001, Mann-Whitney test). The plasma EBV DNA concentrations were statistically significantly higher in patients with detectable urine EBV DNA. The results are shown in FIG. 1.

Figure 2A:
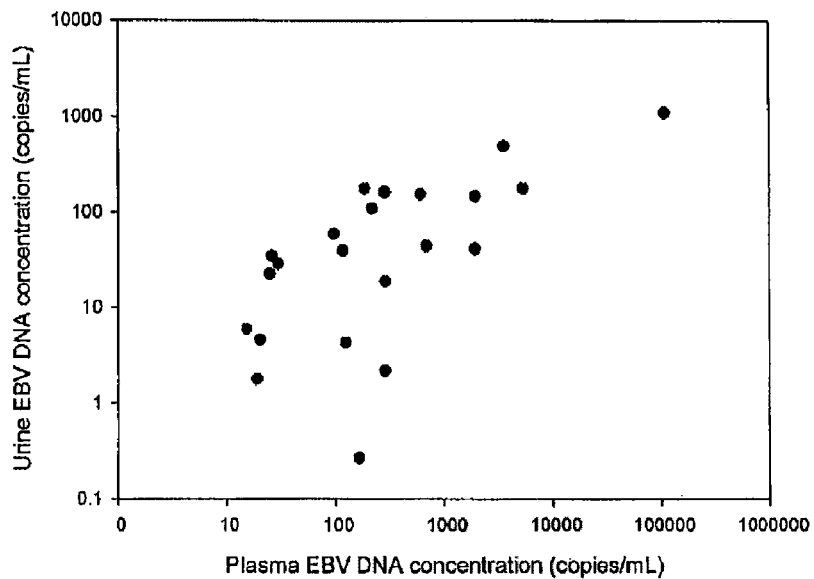
FIG. 2 shows correlation between the plasma EBV DNA and the urine EBV DNA levels in NPC patients with detectable urine EBV DNA, in which (a): the urine EBV DNA concentrations are expressed in copies/mL of urine and (b): the urine EBV DNA concentrations are expressed in copies/mmol of creatinine in the urine.
Figure 2B:
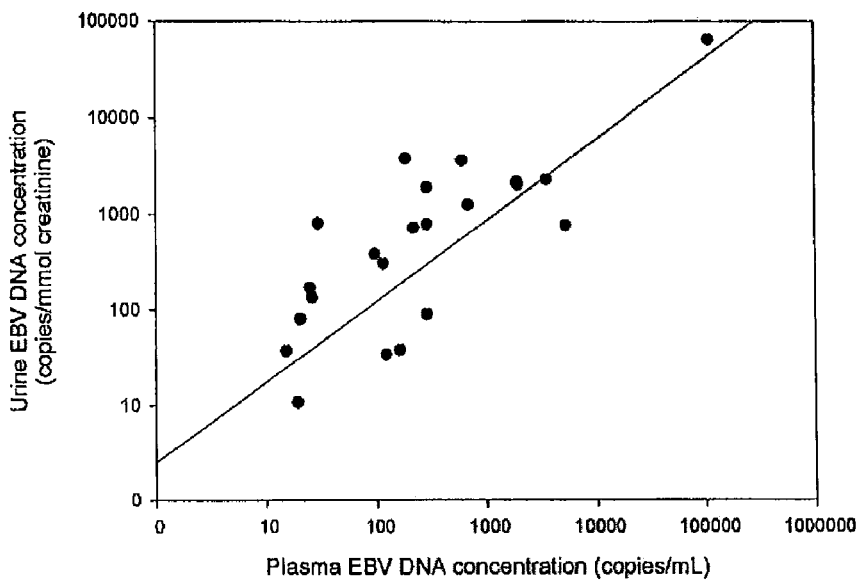

For those patients with detectable urine EBV DNA, we have investigated if there is any correlation between the plasma and urine EBV DNA concentrations. There was a significant positive correlation between the plasma and urine EBV DNA concentrations (r=0.684, p<0.0001, Spearman correlation; FIG. 2a). As the urine concentration of EBV DNA can be affected by the hydration status of a patient, we have corrected the urine concentration of EBV DNA with the urine concentration of creatinine and expressed the urine EBV DNA concentration in copies/mmol creatinine. The positive correlation between the plasma and urine EBV DNA concentrations becomes more prominent when the urine EBV DNA concentrations were corrected with the urine creatinine concentrations (r=0.748, p<0.0001, Spearman correlation; FIG. 2b).

The Presence or the Level of EBV DNA in the Urine Sample being a Useful Indication of Prognosis After a median follow up of 8 months, 3 of the 44 NPC patients had developed clinical recurrence. All the 3 patients had detectable EBV DNA in urine before treatment. In contrast, none of the 22 patients with undetectable urine EBV DNA had developed clinical relapse. As patients with detectable urine EBV DNA had a significantly higher plasma EBV DNA levels, it is expected that urine EBV DNA can also be served as a prognostic marker for post-treatment survival, because it is known a high plasma EBV DNA level is a poor prognostic factor for disease recurrence after treatment. It can be expected the difference in survival probability would become more prominent with the increase in follow up duration.

It should be understood that while the invention has been described in conjunction with the detailed description thereof, the foregoing description is intended to illustrate and not limit the scope of the invention.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

REFERENCES

Chan, A T C, Lo, Y M D, Zee, B, Chan, L Y S, et al. (2002) Plasma Epstein-Barr virus DNA and residual disease after radiotherapy for undifferentiated nasopharyngeal carcinoma. J Natl Cancer Inst 94(21):1614-9.

Chen, C L, Wen, W N, Chen, J Y, Hsu, M M, et al. (1993) Detection of Epstein-Barr virus genome in nasopharyngeal carcinoma by in situ DNA hybridization. Intervirology; 36(2):91-8.

Dickens, P, Srivastava, G, Loke, S L, Chan, C W, et al. (1992) Epstein-Barr virus DNA in nasopharyngeal carcinomas from Chinese patients in Hong Kong. J Clin Pathol; 45(5): 396-7.

Jones, M D and Griffin, B E. (1983) Clustered repeat sequences in the genome of Epstein-Barr virus. Nucleic Acids Res; 11:3919-3937.

Lei, K I, Chan, L Y S, Chan, W Y, Johnson, P J, et al. (2000) Quantitative analysis of circulating cell-free Epstein-Barr virus (EBV) DNA levels in patients with EBV-associated lymphoid malignancies. Br J Haematol 111(1):239-46.

Lo, Y M D, Chan, A T C, Chan, L Y S, Leung, S F, et al. (2000) Molecular prognostication of nasopharyngeal carcinoma by quantitative analysis of circulating Epstein-Barr virus DNA. Cancer Res; 60(24):6878-81.

Lo, Y M D, Chan, L Y S, Lo, K W, Leung, S F, et al. (1999) Quantitative analysis of cell-free Epstein-Barr virus DNA in plasma of patients with nasopharyngeal carcinoma. Cancer Res; 59(6):1188-91.

Lo, Y M D, Chan, W Y, Ng, E K, Chan, L Y, et al. (2001) Circulating Epstein-Barr virus DNA in the serum of patients with gastric carcinoma. Clin Cancer Res; 7(7): 1856-9.

The invention claimed is:

1. A method for diagnosis of an Epstein-Barr virus (EBV)-associated cancer in an individual comprising:
   (a) obtaining a urine sample from the individual; and
   (b) (1) extracting nucleic acids from the urine sample,
       (2) amplifying an EBV-associated nucleic acid sequence using a fragment of the EBV genome present in the acid extracted in step (b)(1) as a template, wherein the amplified EBV-associated nucleic acid sequence is no more than 180 nucleotides in length, and
       (3) detecting the amplified EBV-associated nucleic acid sequence, wherein the presence of the amplified EBV-associated nucleic acid sequence indicates that the individual is suffering from an EBV-associated cancer.

2. The method according to claim 1, wherein said fragment is DNA.

3. The method according to claim 1, further comprising the step of analyzing whether an EBV genome fragment of more than 180 nucleotides is present in the urine sample, wherein the presence of an EBV genome fragment of more than 180 nucleotides in the urine sample indicates that the individual is not suffering from an EBV-associated cancer.

4. The method according to claim 1, wherein two fragments of are quantified in step (b), wherein the two fragments are of different sizes and both are no more than 180 nucleotides, and wherein substantially equal levels of the two fragments in the urine sample indicates that the individual is not suffering from an EBV-associated cancer.

5. The method according to claim 1, wherein a polymerase chain reaction (PCR) assay, a reverse transcriptase polymerase chain reaction (RT-PCR) assay, a real-time quantitative polymerase chain reaction (Q-PCR) assay, or a real-time quantitative reverse transcriptase polymerase chain reaction (Q-RT-PCR) assay is performed in step (b)(2).

6. The method according to claim 5, wherein a pair of primers used in the PCR or Q-PCR assay comprises SEQ ID NO:1 and SEQ ID NO:2 or SEQ ID NO:3 and SEQ ID NO:4.

7. The method according to claim 5, wherein a probe used in the Q-PCR assay has a DNA sequence of SEQ ID NO:5 or SEQ ID NO:6.

8. The method according to claim 1, wherein the EBV-associated cancer is a nasopharyngeal carcinoma (NPC), a natural-killer-cell lymphoma (NK-lymphoma) or a gastric carcinoma.

9. A method for prognosis of an EBV-associated cancer in an individual comprising:
   (a) obtaining a urine sample from the individual; and
   (b) (1) extracting nucleic acids from the urine sample,
       (2) amplifying an EBV-associated nucleic acid sequence using a fragment of the EBV genome present in the nucleic acid extracted in step (b)(1) as a template, wherein the amplified EBV-associated nucleic acid sequence is no more than 180 nucleotides in length, and
       (3) detecting the amplified EBV-associated nucleic acid sequence, wherein the presence of the amplified EBV-associated nucleic acid sequence indicates a poor prognosis of the EBV-associated cancer.

10. The method according to claim 9, wherein said fragment is DNA.

11. The method according to claim 9, wherein a polymerase chain reaction (PCR) assay, a reverse transcriptase polymerase chain reaction (RT-PCR) assay, a real-time quantitative polymerase chain reaction (Q-PCR), or a real-time quantitative reverse transcriptase polymerase chain reaction (Q-RT-PCR) assay is performed in step (b)(2).

12. The method according to claim 11, wherein a pair of primers used in the PCR, RT-PCR, Q-PCR or Q-RT-PCR assay comprises SEQ ID NO:1 and SEQ ID NO:2 or SEQ ID NO:3 and SEQ ID NO:4.

13. The method according to claim 11, wherein a probe used in the Q-PCR or Q-RT-PCR assay has a DNA sequence of SEQ ID NO:5 or SEQ ID NO:6.

14. The method according to claim 9, wherein the EBV-associated cancer is a nasopharyngeal carcinoma (NPC), a natural-killer-cell lymphoma (NK-lymphoma) or a gastric carcinoma.

15. A method for monitoring an EBV-associated cancer in an individual comprising:
 (a) obtaining urine samples from the individual at different time points; and
 (b) (1) extracting nucleic acids from the urine samples,
  (2) amplifying an EBV-associated nucleic acid sequence using a fragment of EBV genome present in the nucleic acid extracted in step (b)(1) as a template, wherein the amplified EBV-associated nucleic acid sequence is no more than 180 nucleotides in length, and
  (3) detecting or quantifying the amplified EBV-associated nucleic acid sequence,
 wherein the presence of an increased level of the EBV-associated nucleic acid sequence in the urine samples indicates the progression of the EBV-associated cancer, and the absence or a decreased level of the EBV-associated nucleic acid sequence in the urine samples indicates the regression of the EBV-associated cancer.

16. The method according to claim 15, wherein step (a) is performed at different time points during a treatment of the EBV-associated cancer of the individual, and the absence or a decreased level of the EBV-associated nucleic acid sequence in the urine samples indicates the effectiveness of the treatment.

17. The method according to claim 15, wherein the EBV-associated nucleic acid is DNA.

18. The method according to claim 15, wherein a polymerase chain reaction (PCR) assay, a reverse transcriptase polymerase chain reaction (RT-PCR) assay, a real-time quantitative polymerase chain reaction (Q-PCR) assay, or a real-time quantitative reverse transcriptase polymerase chain reaction (Q-RT-PCR) assay is performed in step (b)(2).

19. The method according to claim 18, wherein a pair of primers used in the PCR, RT-PCR, Q-PCR or Q-RT-PCR assay comprise SEQ ID NO:1 and SEQ ID NO:2; and SEQ ID NO:3 and SEQ ID NO:4.

20. The method according to claim 18, wherein a probe used in the Q-PCR or Q-RT-PCR assay has a DNA sequence of SEQ ID NO:5 or SEQ ID NO:6.

21. The method according to claim 15, wherein the EBV-associated cancer is a nasopharyngeal carcinoma (NPC), a natural-killer-cell lymphoma (NK-lymphoma) or a gastric carcinoma.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Forward primer for EBV DNA

<400> SEQUENCE: 1
cccaacactc caccacacc                                                   19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for EBV DNA

<400> SEQUENCE: 2
tcttaggagc tgtccgaggg                                                  20

<210> SEQ ID NO 3
<211> LENGTH: 21
<212> TYPE: DNA
<213> ORGANISM: Artificial Sequence
<220> FEATURE:
<223> OTHER INFORMATION: Forward primer for EBV DNA

<400> SEQUENCE: 3
cccaggcaca cactacacac a                                                21

<210> SEQ ID NO 4
<211> LENGTH: 20
<212> TYPE: DNA
<213> ORGANISM: Artificial Sequence
```

```
-continued

<220> FEATURE:
<223> OTHER INFORMATION: Reverse primer for EBV DNA

<400> SEQUENCE: 4
tcttaggagc tgtccgaggg                                              20

<210> SEQ ID NO 5
<211> LENGTH: 27
<212> TYPE: DNA
<213> ORGANISM: Artificial Sequence
<220> FEATURE:
<223> OTHER INFORMATION: Probe for EBV DNA

<400> SEQUENCE: 5
cacacactac acacacccac ccgtctc                                      27

<210> SEQ ID NO 6
<211> LENGTH: 14
<212> TYPE: DNA
<213> ORGANISM: Artificial Sequence
<220> FEATURE:
<223> OTHER INFORMATION: Probe for EBV DNA

<400> SEQUENCE: 6
cacccgtctc aggg                                                    14
```